US006938832B2

(12) United States Patent
Sada

(10) Patent No.: US 6,938,832 B2
(45) Date of Patent: Sep. 6, 2005

(54) SCENT STRIP

(76) Inventor: David P. Sada, 1206 S. First, Harlingen, TX (US) 78550

(*) Notice: Subject to any disclaimer, the term of this patent is extended or adjusted under 35 U.S.C. 154(b) by 59 days.

(21) Appl. No.: 10/265,364

(22) Filed: Oct. 7, 2002

(65) Prior Publication Data

US 2004/0065748 A1 Apr. 8, 2004

(51) Int. Cl.$^7$ ................................................ A24F 25/00
(52) U.S. Cl. .......................................... 239/41; 239/56
(58) Field of Search ............................ 239/34, 41, 42, 239/43, 44, 53, 54, 56, 57, 55

(56) References Cited

U.S. PATENT DOCUMENTS

| 2,615,754 | A |   | 10/1952 | Lindenberg |
|---|---|---|---|---|
| 4,071,624 | A |   | 1/1978 | Grunwell et al. |
| 4,277,024 | A |   | 7/1981 | Spector |
| 4,283,011 | A |   | 8/1981 | Spector |
| 4,285,468 | A |   | 8/1981 | Hyman |
| 4,544,592 | A |   | 10/1985 | Spector |
| 4,629,604 | A | * | 12/1986 | Spector ....................... 422/124 |
| 4,695,434 | A | * | 9/1987 | Spector ....................... 422/116 |
| 4,744,514 | A | * | 5/1988 | Gadoua ......................... 239/36 |
| 4,752,496 | A |   | 6/1988 | Fellows et al. |
| 4,809,912 | A | * | 3/1989 | Santini ........................ 239/60 |
| 4,874,129 | A | * | 10/1989 | DiSapio et al. ............... 239/36 |
| 5,150,722 | A | * | 9/1992 | Rutherford .................. 131/335 |
| 5,272,134 | A |   | 12/1993 | Berliner |
| 5,460,787 | A | * | 10/1995 | Colon ......................... 422/123 |
| 5,809,577 | A | * | 9/1998 | Getz ............................. 2/406 |
| 5,899,382 | A | * | 5/1999 | Hayes et al. .................. 239/56 |
| 5,951,353 | A | * | 9/1999 | Moore ......................... 446/46 |
| 5,971,143 | A | * | 10/1999 | Yoshioka ..................... 206/307 |
| 6,039,488 | A | * | 3/2000 | Krawczyk et al. ........... 401/132 |
| 6,234,455 | B1 |  | 5/2001 | Wittek |
| 6,296,913 | B1 | * | 10/2001 | D'Andrade ................ 428/40.1 |
| 6,328,287 | B2 |  | 12/2001 | Wittek |
| 6,581,915 | B2 | * | 6/2003 | Bartsch et al. ................ 261/26 |
| 2002/0114744 | A1 | * | 8/2002 | Chiao et al. ................ 422/124 |

FOREIGN PATENT DOCUMENTS

JP          410101022 A  *  4/1998

* cited by examiner

Primary Examiner—Nohammad M. Ali
(74) Attorney, Agent, or Firm—Richard C. Litman

(57) ABSTRACT

A scent strip for use with digital entertainment media contains a volatile mixture of a detectable scent and an imperceptible pheromone which is adhesively attached to a digital entertainment medium package, e.g., a CD/DVD case or VHS cassette, or to a print medium, e.g., business card or magazine. The strip includes a peelable cover layer, that, when removed, releases the contained volatile mixture causing a desired modification in behavior, such as increasing a person's libido. The cover layer can be removed in accordance with written instructions provided with the strip indicating a cue, e.g., during payback of the medium, when the cover layer should be removed, e.g., during a particular scene in a movie.

5 Claims, 4 Drawing Sheets

SCENT STRIP

BACKGROUND OF THE INVENTION

1. Field of the Invention

The present invention relates generally to scent strips. More particularly, the inventive strip contains a volatile mixture of a perceptible scent, such as a citrus odor, and a substantially imperceptible behavior-modifying ingredient, such as a pheromone. The strip is provided with a pressure sensitive adhesive on one side for adhering the strip to a surface, and a peelable cover layer on the opposite side to be removed to release the volatile mixture. The strip can be adhered to the surface of cases for entertainment media, such as VHS tape cassettes or DVD disc cases, or to other surfaces, such as novelty items, business cards and magazines. The peelable cover layer is removed by the user during playback of the medium when a specified cue occurs, thereby allowing the user to detect the scent and to experience the effects of the pheromone.

2. Description of the Related Art

The invention is generally related to scent strips. More particularly, the inventive strip contains a volatile mixture of a perceptible scent and a substantially imperceptible pheromone which may have a the effect of modifying normal behavioral patterns.

U.S. Pat. No. 2,615,754 issued to Lindenberg, on Oct. 28, 1952, teaches a perfume-containing sachet that is adhesively attached to clothes. U.S. Pat. No. 4,071,624, issued to Grunwell et al. on Jan. 31, 1978, teaches a pheromone composition. The disclosure of the Grunwell patent is hereby incorporated by reference. U.S. Pat. No. 4,277,024, issued to Spector on Jul. 7, 1981, teaches a self-stick aroma-dispensing strip containing a fragrance and an insect-repellent.

U.S. Pat. No. 4,283,011, issued to Spector on Aug. 11, 1981, teaches an aromatic, adhesively-applied strip containing a scent that matches the expected scent corresponding to an image on which the strip is adhered. U.S. Pat. No. 4,285,468, issued to Hyman on Aug. 25, 1981, teaches a strip containing volatiles and a peelable protective layer that is removed to expose the volatiles. U.S. Pat. No. 4,544,592, issued to Spector on Oct. 1, 1985, teaches an aroma-generating capsule.

U.S. Pat. No. 4,752,496, issued to Fellows et al. on Jun. 21, 1988, teaches a cosmetics-containing strip that is released when a protective peelable layer is removed, and is applied to various print media, such as magazine inserts. U.S. Pat. No. 5,272,134, issued to Berliner on Dec. 21, 1993, teaches a fragrance and pheromone composition. U.S. Pat. Nos. 6,234,455 and 6,328,287, issued to Wittek on May 22, 2001 and Dec. 11, 2001, respectively, teach a "scent player" in which a CD-style disc with several individual scent-containing pockets releases the scents according to a timer or program.

Although scent strips are generally taught in the prior art, there is a need for a scent strip containing a volatile mixture of a detectable scent and a behavior-modifying ingredient, such as a pheromone. Also, there is a need for a scent strip as described in which the strip modifies the mood or behavior of a user during playback of an entertainment medium in accordance with written directions that specify a cue signifying when to release the volatile mixture.

Alternatively, the strip can be adhered to print media, such as business cards, magazines, etc., or to novelty items with instructions to release the volatile mixture in order to obtain a desired mood or behavior modification at a specified time.

None of the above inventions and patents, taken either singly or in combination, is seen to describe the instant invention as claimed. Thus a scent strip for use with digital entertainment, print media, or novelty items solving the aforementioned problems is desired.

SUMMARY OF THE INVENTION

The present invention is a scent strip which contains a volatile mixture of a perceptible scent and a substantially imperceptible pheromone. The strip is provided with a pressure sensitive adhesive on one side to adhere the strip to the surface of entertainment and print media, and a peelable cover layer on the opposite side to be removed at an appropriate time to release the volatile mixture. The strip can be adhered to the surface of cases for entertainment media, such as VHS tape cassettes or DVD cases. Alternatively, the strip can be applied to the surface of print media or novelty items, such as business cards and magazines with instructions when to remove the peelable cover layer to release the volatile mixture to obtain a desired behavior-modifying or mood-altering effect at a desired time.

Before playing back entertainment media, the user reads the instructions provided with the strip to determine when to remove the protective cover layer to release the mixture to permeate the immediate space surrounding the user so that the user can inhale the mixture and receive maximum benefit from the exposure. The instructions may specify a particular cue when the protective cover should be removed to release the volatile mixture. The cue might be a particular sound track or a particular scene in a movie. The mixture is intended to create a desired modification in behavior or mood, including enhancing libido or other stimulation.

Accordingly, it is a principal object of the invention to provide a scent strip including a behavior-modifying ingredient, such as a pheromone, for use with digital entertainment, print media, and novelty items.

It is another object of the invention to provide the above scent strip with a peelable cover layer which is removed at a specified time during playback of the entertainment medium.

Still another object of the invention is to provide a scent strip having a pressure adhesive layer for adhering the strip to the casing of the medium, e.g., a DVD case.

Still another object of the invention is to provide a sent strip as above which is adhered to the surface of a print medium, such as a business card or magazine, with instructions when to release the volatile mixture to elicit a modification in mood or behavior at a desired time.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is directed to a strip containing a perceptible scent and a substantially imperceptible pheromone, preferably a human pheromone, which may have behavior-modifying or mood-altering effects. The strip can be adhered to the cases of digital entertainment media, to print media, to novelty items, etc.

Figure 1:
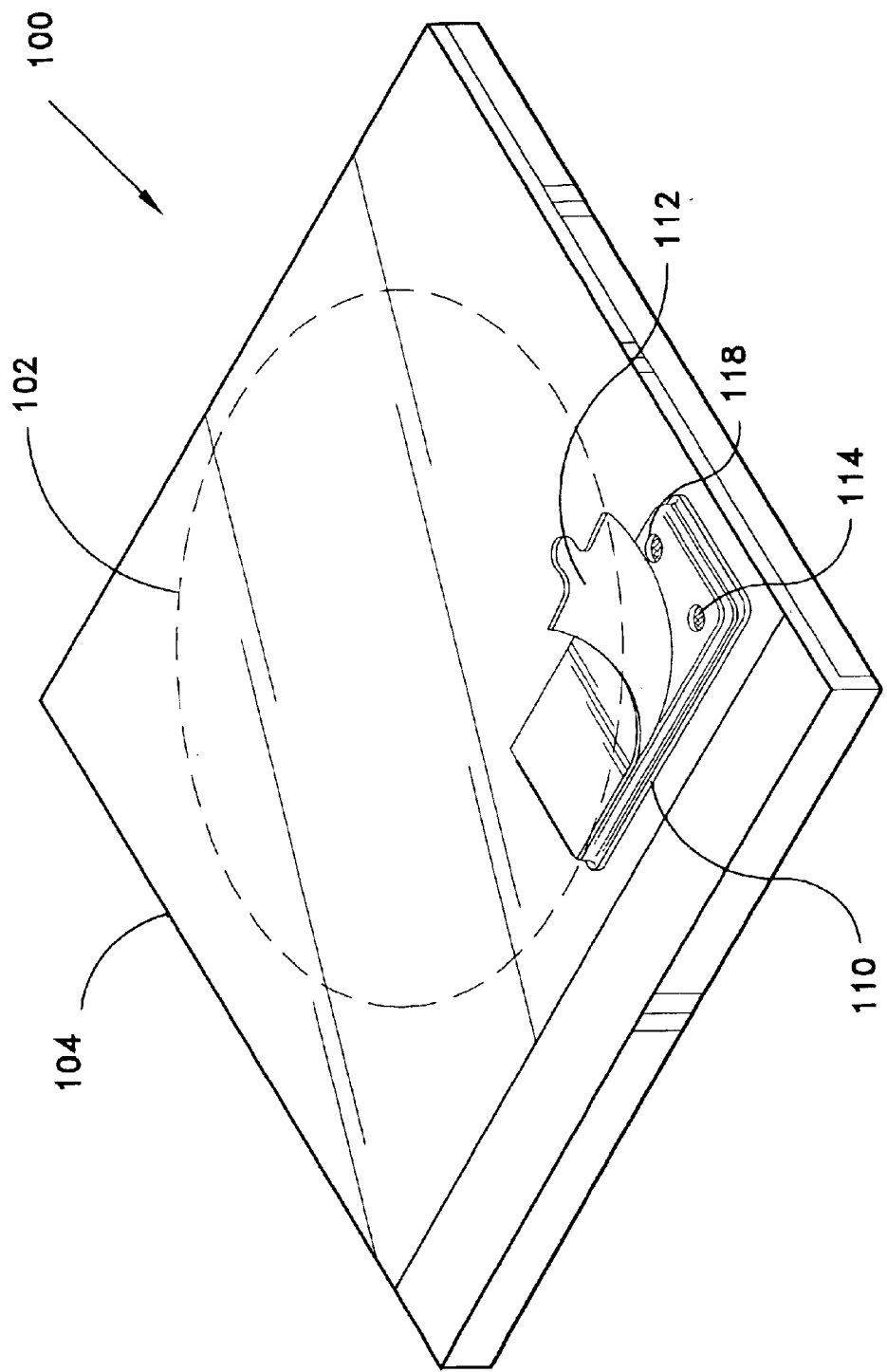
FIG. 1 is an environmental, perspective view of a scent strip applied to a DVD jewel case according to the present invention.

FIG. 1 shows an overview 100 of the inventive scent strip attached to a jewel case 104 containing a DVD (digital video disc) 102. The DVD disc is a well-known type of media that typically includes digital information, specifically a movie or similar video file or files that can be read by a DVD player and viewed on a monitor. The scent strip 110 includes a peelable cover layer 112. The peelable layer 112 is removed to release the volatile mixture from the porous material 114 through vent holes 118.

The volatile mixture includes a scent, such as a citrus or other detectable odor or fragrance, and a behavior-modifying ingredient ("behavior-modifying", for purposes of the present application, means influencing a specific pattern of behavior or releasing a specific reaction of behavior in the percipient), such as a pheromone, preferably a human pheromone, i.e., a substance secreted by humans. The pheromone can be, e.g., an androstenone for enhancing the libido, or other behavior-modifying composition. The purpose of the behavior-modifying ingredient is to elicit a desired behavioral response by the user while using the media. Preferably, the media is provided with readable instructions that indicate the appropriate time for the user to peel off the protective peelable top layer 112 to "activate" the scent strip, i.e., to release the volatile mixture. The user then inhales the mixture and experiences the desired behavior-modification, such as increased libido or other stimulation. For example, the user may be instructed to peel the protective layer 112 during a specified scene in a movie or during a specified sound track. The scene may be erotic, in which case the behavior-modifying ingredient may deliberately elicit an increased libido or motivate passion, sexual desire, or romance in the viewer or viewers.

Figure 2:
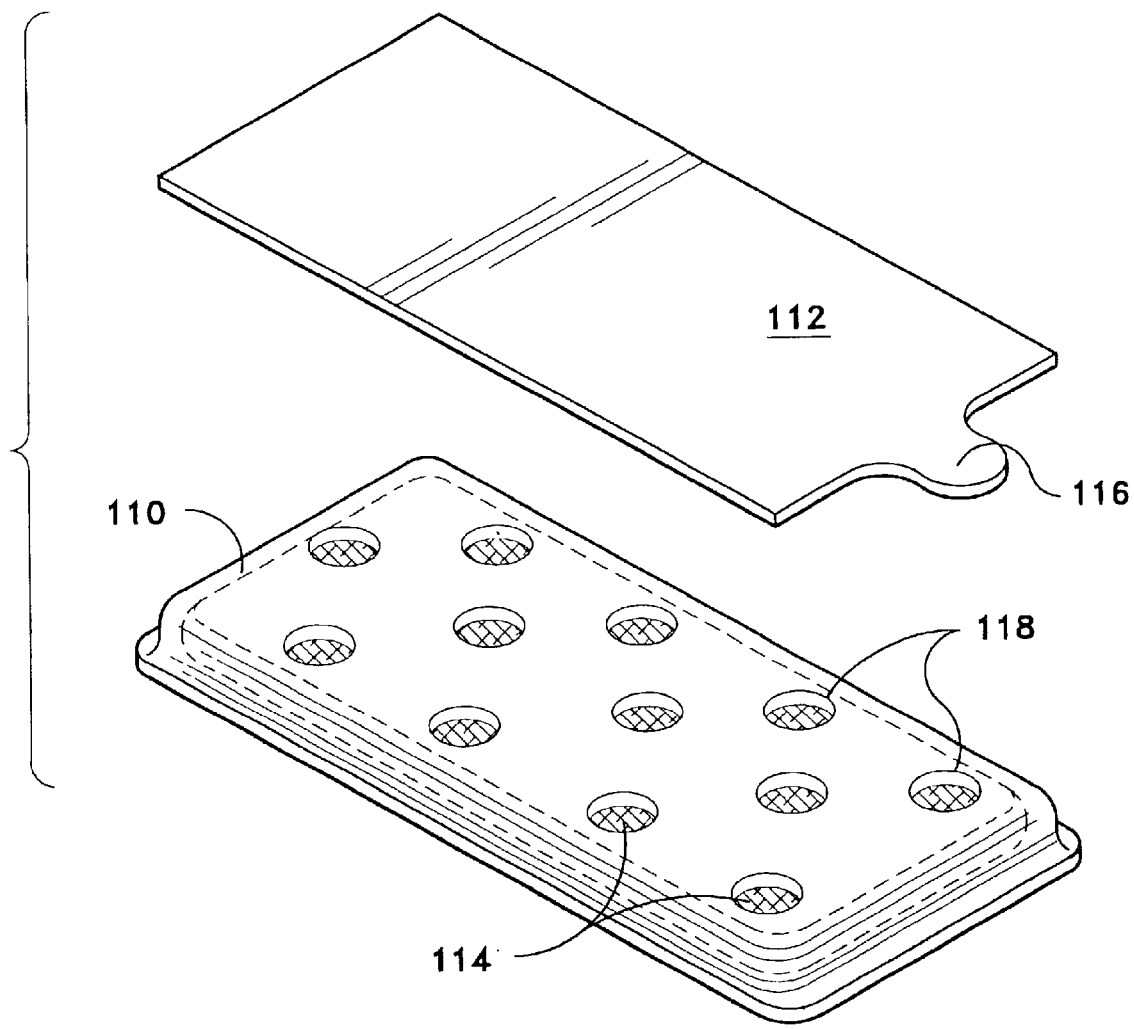
FIG. 2 is an exploded view of the scent strip showing circular vent holes and peelable layer.

FIG. 2 shows an exploded detailed view of the scent strip 110, showing the protective peelable cover layer 112 and a tab 116 which can be used by a user to grasp and peel back the cover layer 112 when a cue occurs as specified in written instructions provided with the strip. When the protective layer 112 is removed, the scent strip 110 is "activated" by releasing the volatile mixture through holes 118, from the porous material 114 that contains the mixture. The cover 112 itself, and the casing in which holes 118 are defined, is made from a material impermeable to both the odor producing scent and the pheromone, and which preserves the volatile material in the porous media 114 until the cover 112 is pulled open.

Figure 3:
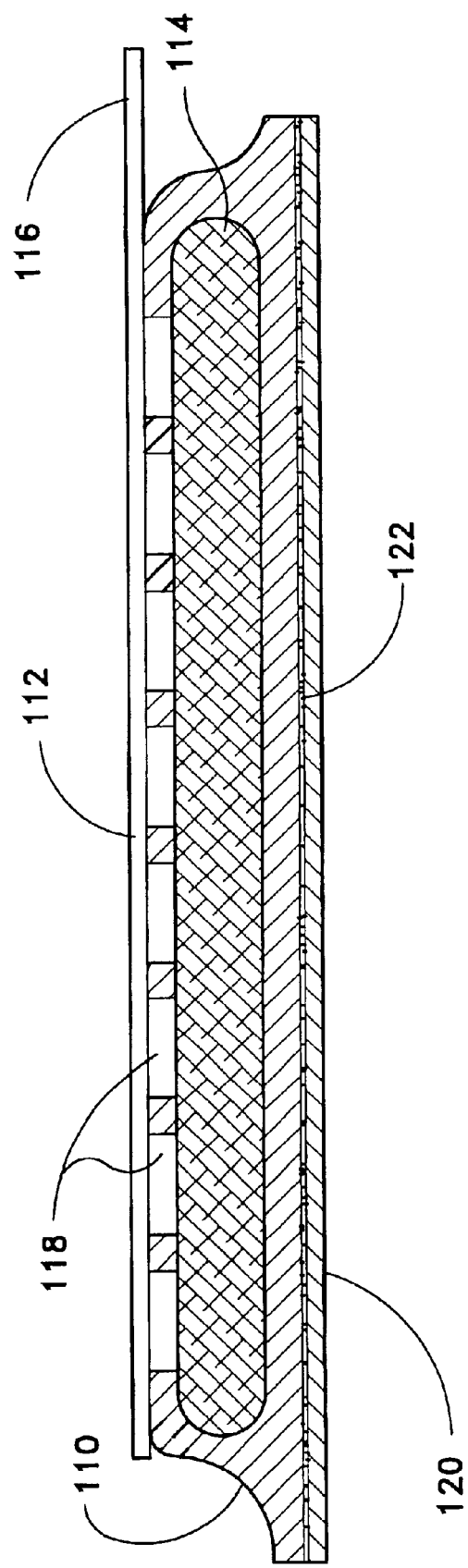
FIG. 3 is a detailed elevational view of the scent strip, partially in section.

FIG. 3 shows a detailed elevational view of the scent strip 110 showing the protective cover layer 112 in place on the strip 110. The porous material 114 containing the volatile mixture can be a cloth or plastic material, e.g., sponge, etc. On the bottom of the strip 110 shown in FIG. 3, a protective removable layer 120 is shown covering adhesive layer 122. Layer 120 is removed in order to adhere the scent strip 110 to any desired product, e.g., DVD or CD jewel cases, video cassette packages, print media, novelty items, etc. The scent strip 110 in this case can be adhered to the casing of any media, e.g., for DVD, VHS cassette, etc., along with readable instructions for the user, indicating when to remove the peelable layer 112 to release the mixture.

Figure 4:
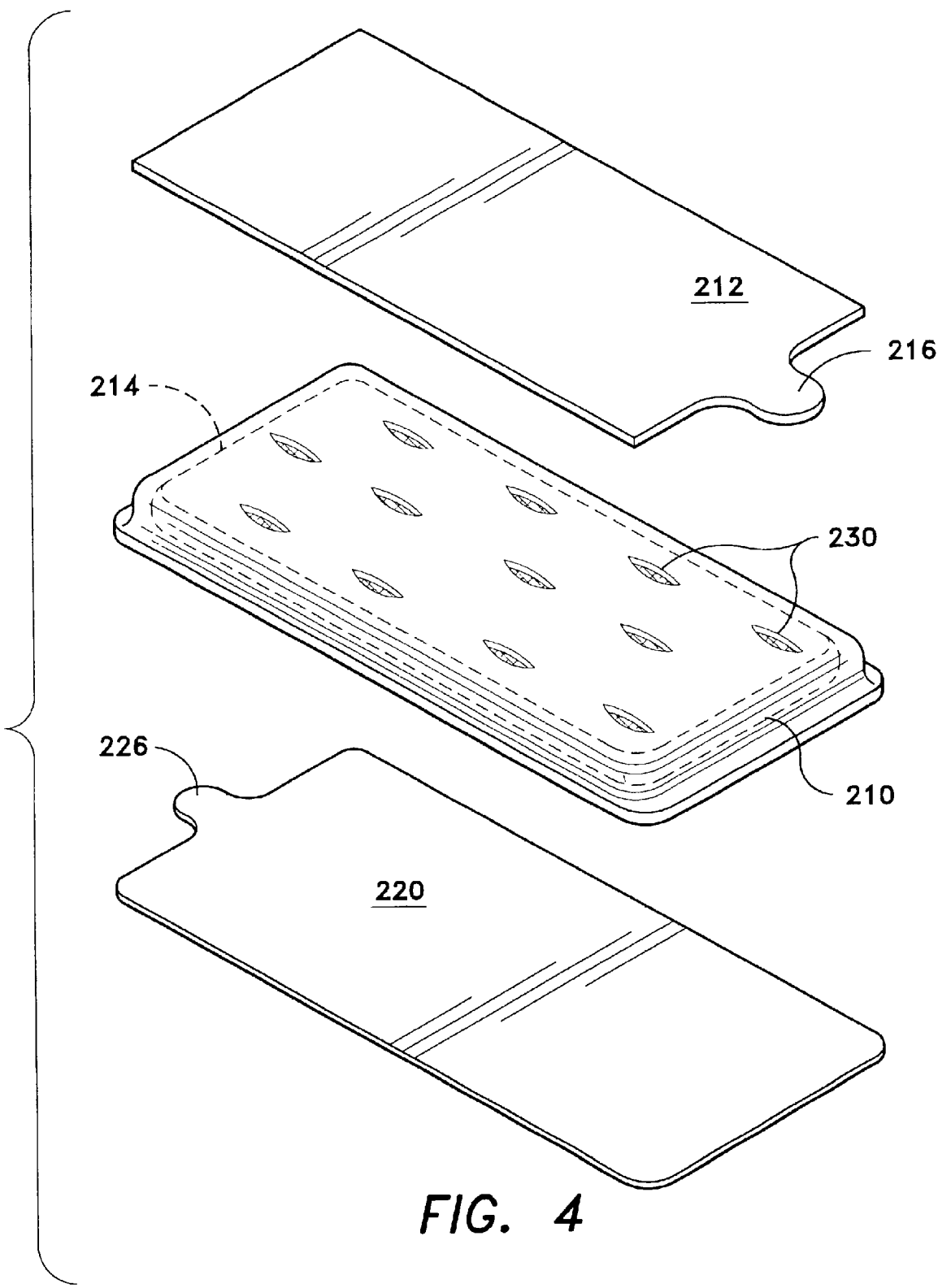
FIG. 4 is an exploded view of the scent strip showing slits and a peelable top and peelable bottom layer.

FIG. 4 shows an exploded view of the scent strip 210 with slits 230. The porous material 214 is encapsulated inside the strip and is protected by a peelable cover layer 212. Cover layer 212 includes a grip tab 216. Peelable bottom layer 220 has its own grip tab 226. The bottom layer 220 is removed to expose a layer of adhesive to apply the strip to the surface of a media, such as the casing of a DVD.

The written instructions may specify a cue that occurs during playback of the medium. When the cue occurs, the user removes the protective peelable cover layer to release the volatile mixture. The user then smells the perceptible scent, e.g., a citrus or other odor, and experiences the desired modified behavior, such as increased libido or other stimulation caused by the substantially imperceptible behavior-modifying or mood-altering ingredient.

When the strip is applied to the surface of print media, e.g., by adhering to a business card or a magazine, the strip is provided with instructions indicating an appropriate time to release the volatile mixture. The user then inhales the volatile mixture to smell the scent and experience the effects of the behavior-modifying or mood-altering ingredient.

It is to be understood that the present invention is not limited to the embodiments described above, but encompasses any and all embodiments within the scope of the following claims.

I claim:

1. A scent strip comprising:
   a volatile composition, wherein the composition is a mixture of a detectable scent and a substantially imperceptible behavior-modifying ingredient;
   a layer of porous material, the volatile composition being carried in the layer porous material;
   a casing made from a material impermeable to said volatile composition, the casing having a top face and a bottom face, the top face having a plurality of apertures defined therein, the bottom face having a layer of adhesive attached thereto adapted for adhering the casing to a package; and
   a cover removably attached to the top surface of the casing, the cover being made from a material impermeable to said volatile composition and extending over the apertures defined in the top face;
   a digital entertainment medium; and
   a package, said digital entertainment media being contained within said package;
   wherein the bottom face of said casing is attached to said package by said adhesive layer, and the behavior-modifying ingredient includes a human pheromone.

2. The scent strip of claim 1, wherein the pheromone is an androstenone capable of enhancing libido.

3. A scent strip comprising:
   a volatile composition, including a substantially imperceptible behavior-modifying ingredient;
   wherein the composition is a mixture of a detectable scent and the substantially imperceptible behavior-modifying ingredient;
   whereby the behavior-modifying ingredient includes the human pheromone androstenone for enhancing libido;
   a layer of porous material, the volatile composition being carried in the layer porous material;

a casing made from a material impermeable to said volatile composition, the casing having a top face and a bottom face, the top face having a plurality of apertures defined therein, the bottom face having a layer of adhesive attached thereto adapted for adhering the casing to a package;

a cover removably attached to the top surface of the casing, the cover being made from a material impermeable to said volatile composition and extending over the apertures defined in the top face;

a digital entertainment medium; and a package, said digital entertainment media being contained within said package;

wherein the bottom face of said casing is attached to said package by said adhesive layer.

4. A scent strip comprising:

a volatile composition, including a substantially imperceptible behavior-modifying ingredient;

wherein the composition is a mixture of a detectable scent and the substantially imperceptible behavior-modifying ingredient;

whereby the behavior-modifying ingredient includes the human pheromone androstenone for enhancing libido;

a layer of porous material, the volatile composition being carried in the layer porous material;

a casing made from a material impermeable to said volatile composition, the casing having a top face and a bottom face, the top face having a plurality of apertures defined therein, the bottom face having a layer of adhesive attached thereto adapted for adhering the casing to a package; and a cover removably attached to the top surface of the casing, the cover being made from a material impermeable to said volatile composition and extending over the apertures defined in the top face.

5. The scent strip of claim 4 further comprising:

a digital entertainment medium; and a package, said digital entertainment media being contained within said package;

wherein the bottom face of said casing is attached to said package by said adhesive layer.

* * * * *